United States Patent [19]

Sweeney

[11] 4,181,662
[45] Jan. 1, 1980

[54] 2-PYRROLIDONE PRODUCTION

[75] Inventor: W. Alan Sweeney, Larkspur, Calif.

[73] Assignee: Chevron Research Company, San Francisco, Calif.

[21] Appl. No.: 891,430

[22] Filed: Mar. 29, 1978

[51] Int. Cl.$^2$ ............................................ C07D 207/26
[52] U.S. Cl. ............................................ 260/326.5 FN
[58] Field of Search ............................. 260/326.5 FN

[56] References Cited

U.S. PATENT DOCUMENTS

| | | | |
|---|---|---|---|
| 3,644,402 | 2/1972 | Takagi et al. | 260/326.5 FN |
| 4,036,836 | 7/1977 | Greene | 260/326.5 FN |
| 4,042,599 | 8/1977 | Greene | 260/326.5 FN |

Primary Examiner—Jose Tovar
Attorney, Agent, or Firm—D. A. Newell; T. G. DeJonghe

[57] ABSTRACT

A process for production of 2-pyrrolidone which comprises (a) contacting succinonitrile with water at a temperature between 150° and 300° C. and a pressure between 50 and 10,000 psig to thereby hydrolyze succinonitrile and (b) contacting the hydrolyzed succinonitrile with hydrogen in the presence of a heterogeneous hydrogenation catalyst and at a temperature between 200° and 300° C. and a pressure between 100 and 10,000 psig to thereby obtain 2-pyrrolidone.

7 Claims, No Drawings

2-PYRROLIDONE PRODUCTION

BACKGROUND OF THE INVENTION

The present invention is directed to a process for producing 2-pyrrolidone from succinonitrile. The 2-pyrrolidone may be used to produce polypyrrolidone (nylon-4).

Various methods have been described for producing 2-pyrrolidone. For example, U.S. Pat. No. 3,644,402 discloses a process for producing 2-pyrrolidone by contacting succinonitrile with hydrogen under pressure in the presence of a hydrogenating catalyst and a nitrogen-containing organic solvent at a temperature of 80°–200° C. for a period of time less than 3.7 minutes followed by a hydrolyzing step carried out by adding water or aqueous ammonia solution into the reaction mixture from the previous step and then heating the reaction mixture at a temperature of from 200°–300° C.

Belgian Pat. No. 839,091 also discloses a process for producing 2-pyrrolidone from such succinonitrile wherein the reaction steps are hydrogenation followed by hydrolysis. According to the process of the Belgian patent, succinonitrile is subjected to hydrogenation in the liquid phase in the presence of ammonia at a partial hydrogen pressure between 1 and 50 atmospheres and the reaction product obtained is treated in the liquid phase at elevated temperature with water. Yields disclosed in the examples of the Belgian patent range from 78–86 mol percent.

Several patents have described a one-step method for conversion of succinonitrile to 2-pyrrolidone such as in U.S. Pat. Nos. 3,095,423; 3,781,298; 3,966,763; and 4,036,836. U.S. Pat. No. 3,095,423 discloses yields of about 25 percent in a process where succinonitrile is heated in the presence of water at a temperature of 20°–200° C. and in the presence of a hydrogenation catalyst and hydrogen under a pressure of at least 500 psig. This patent also discloses that ammonia presence in the reaction zone is advantageous as it suppresses the formation of secondary amines. Catalysts disclosed in the 3,095,423 patent include ruthenium oxide, platinum oxide, supported noble metal catalysts such as platinum and palladium on carbon or alumina, Raney nickel and Raney cobalt.

The aforementioned U.S. Pat. No. 3,781,298 discloses the reaction of succinonitrile with hydrogen in the absence of added ammonia and in the presence of a Raney cobalt catalyst at a temperature of 250°–300° C. and a hydrogen pressure of about 2000–3500 psig to obtain 2-pyrrolidone. A yield of about 62 mol percent is reported in the U.S. Pat. No. 3,781,298.

The aforementioned U.S. Pat. No. 3,966,763 discloses a one-step hydrogenation process in the presence of water for converting succinonitrile to 2-pyrrolidone wherein a promoter such as added 2-pyrrolidone is used and yields of 38–56 percent are obtained.

Another one-step process for conversion of succinonitrile to 2-pyrrolidone is disclosed in U.S. Pat. No. 4,036,836 which patent reports yields of 46–59.5 mol percent using a nickel boride catalyst.

Succinic acid and maleic anhydride have also been disclosed as feed materials for the production of gammabutyrolactone, which may be reacted with ammonia to produce 2-pyrrolidone. U.S. Pat. No. 3,890,361 discloses conversion of succinic acid, succinic anhydride, maleic acid or maleic anhydride to gamma-butyrolactone by contacting the feed with hydrogen in the presence of a hydrogenation catalyst consisting of a uniform mixture of nickel, molybdenum, and a third component selected from barium and thallium. The hydrogenation is carried out at 180°–300° C. and a pressure of 30–200 atmospheres. As disclosed in U.S. Pat. No. 3,975,400, gamma-butyrolactone may be converted to the corresponding lactam, that is, 2-pyrrolidone, by treatment with ammonia in the presence or absence of water at 180°–340° C. and pressures of 25–280 atmospheres.

One-step conversion of succinic acid or maleic anhydride to 2-pyrrolidone is disclosed in U.S. Pat. Nos. 3,812,148; 3,812,149; and 3,884,936. The U.S. Pat. No. 3,812,148 discloses reacting succinic acid or its precursor with hydrogen and ammonia in an aqueous system at a mol ratio of ammonia to succinic acid of from 1.3:1 to 1.7:1, a temperature of 250° to 275° C., a pressure of 1500 to 2000 psig, and in the presence of a ruthenium on alumina catalyst. The U.S. Pat. No. 3,812,149 is similar except that a rhodium catalyst is used. Both of these patents report mol percent yields of 2-pyrrolidone up to 90 or 95 percent. U.S. Pat. No. 3,884,936 also discloses a one-step preparation of 2-pyrrolidone by reaction of maleic acid or maleic anhydride with hydrogen and ammonia in an aqueous system with a mol ratio of ammonia to maleic acid or anhydride of from 1:1 to 1.2:1 and using a palladium on carbon catalyst.

The present invention, which is a two-step process for the production of 2-pyrrolidone, involves a nitrile hydrolysis step as will be described in more detail below. The hydrolysis of nitrile groups has been disclosed in the art (see for example Morrison and Boyd, Organic Chemistry, second edition, 1966, Page 588).

SUMMARY OF THE INVENTION

According to the present invention, a process is provided for producing 2-pyrrolidone which process comprises (a) contacting succinonitrile with water at a temperature between 150° and 300° C. and a pressure between 50 and 10,000 psig to thereby hydrolyze succinonitrile and (b) contacting the hydrolyzed succinonitrile with hydrogen in the presence of a heterogeneous hydrogenation catalyst and at a temperature between 200° and 300° C. and a pressure between 100 and 10,000 psig to thereby obtain 2-pyrrolidone.

Among other factors, the present invention is based on my finding that, starting with a succinonitrile feed, hydrolysis followed by hydrogenation in accordance with the present invention produces a high yield of 2-pyrrolidone. The high yield from this process is particularly unexpected in view of the fact that the sequence of steps used in the present invention, that is, hydrolysis followed by hydrogenation, is the reverse of the two-step sequence taught by the prior art for obtaining 2-pyrrolidone from succinonitrile.

Preferably, the hydrolysis of the succinonitrile in accordance with the present invention is carried out at a temperature between about 180° and 250° C. A temperature of about 190°–230° C. is particularly preferred. Preferred pressures for the hydrolysis step are sufficient to maintain water in the liquid phase present in the hydrolysis reaction zone at the elevated temperature used for hydrolysis. Usually the pressure is maintained between 100 and 1000 psig.

Preferred molar ratios for water to succinonitrile in the feed to the hydrolysis step are between about 200:1 and 2:1, more preferably between about 30:1 and 5:1.

Residence time for the hydrolysis step may be 0.1 to 20 hours, preferably 0.25 to 4 hours.

The hydrolysis step can be catalyzed by added acids or bases. However, strong acids or bases tend to be quenched in activity by the carboxyl and ammonium products of the hydrolysis. Also their presence complicates product recovery. Therefore, it is preferred to not use these catalysts. Some advantage in hydrolysis rate can be obtained by adding ammonia or carboxyl-containing compounds to alter the equal proportion of these weak basic and acidic groups which are formed in the hydrolysis reaction. This can be achieved in two simple ways: (1) some ammonia, which is a net by-product from the two-step process, can be recycled to the hydrolysis step, or (2) some hydrolysis product can be recycled to that zone after stripping out some ammonia.

The hydrolysis conditions are preferably maintained so that at least one of the nitrile groups of succinonitrile is converted to a carboxyl type group, i.e., to an amide or a carboxyl group or its ammonium salt. The other nitrile group of the succinonitrile can remain unreacted for a reaction product which is suitable for the second step of the present invention, that is, the hydrogenation/cyclization step.

In accordance with this invention, preferably the hydrolysis conditions are such that at least a portion of the succinonitrile is converted to succinic acid-type products, such as various amides and ammonium salts. Conditions suitable for converting a relatively large portion of the succinonitrile to the succinic acid compounds involve a higher temperature or longer times than is used for conversion of only one of the nitrile groups of succinonitrile to a carboxyl-type group.

For the hydrogenation step, the temperature may range from about 20° C. to 300° C. depending on the product of the hydrolysis step. In one embodiment of this invention, the hydrolysis mixture would be conducted through a two-stage hydrogenation. In the first low temperature stage, at about 20°–150° C., any residual nitrile groups are hydrogenated. In the second stage, at about 200°–300° C., carboxyl type groups are hydrogenated and ring closure to 2-pyrrolidone occurs. If relatively mild hydrolysis conditions were employed and a considerable number of nitrile groups remained, the two-step approach may be desired. If more severe hydrolysis was performed, the low temperature stage may be unnecessary. In either case, the final hydrogenation temperature preferably is between about 200°–300° C. More preferably the temperature is between about 210°–280° C., most preferably about 215°–255° C. A temperature of about 235° C. has been found particularly suitable for the hydrogenation step of the present invention.

Preferred pressure for the hydrogenation step is between 100 and 10,000 psig, preferably about 200–2500 psig. The pressure preferably is sufficient to maintain water and ammonia in the liquid phase.

The feed to the hydrogenation step of the present invention can be the total effluent mixture from the preceeding hydrolysis step of the process or a portion of the ammonia and/or water may be removed before feeding the hydrolysis step reaction product to the hydrogenation step. Preferably, the entire mixture or substantially the entire mixture resulting from the hydrolysis step is fed to the hydrogenation step of the present invention.

In the hydrolysis step, ammonia will be formed to the extent that the nitrile groups of succinonitrile are converted to carboxyl groups. Thus, the theoretical maximum amount of ammonia which can be formed in the hydrolysis step is 2 mols per mol of succinonitrile feed to the hydrolysis step. If the succinonitrile is hydrolyzed only as far as the amide, which usually will not be the case, then it is preferred to add some ammonia to the hydrogenation zone feed as there will be little or no ammonia in the hydrolysis step effluent which is typically fed to the hydrogenation zone. The hydrogenation reaction zone conditions preferably are maintained so that at least 0.10 mol, and usually no more than 5.0 mols of ammonia, are present per mol of succinic reactant. More preferably the amount of ammonia is between 0.25 and 2 mols of ammonia per mol of succinic reactant.

The term "succinic reactant" is used in a general sense to cover the hydrolyzed succinonitrile, whether partially or completely hydrolyzed and whether it contains carboxyl or amide groups. If the succinic reactant in the hydrogenation step is in the form of an amide, ammonia will be evolved in the hydrogenation/cyclization reaction by which 2-pyrrolidone is produced in the hydrogenation zone. Thus, the ammonia content in the hydrogenation zone is maintained not only by ammonia which may be fed to the hydrogenation step as part of the reaction effluent of the hydrolysis step, or as a separately added ammonia stream, but also the ammonia which may be generated from the feed to the hydrogenation reaction zone while the feed is being converted to 2-pyrrolidone.

Preferably, the hydrogenation reaction is carried out in liquid phase with water being the liquid medium. The mol ratio of water to succinic reactant preferably is between 1:1 and 400:1, more preferably between 2:1 and 50:1 in the hydrogenation step reaction zone. Similar to the situation with ammonia, water may be added separately to the reaction zone if desired and also the amount of water in the reaction zone will be increased by the conversion of the succinic reactant to 2-pyrrolidone. In the case of conversion of succinic acid to 2-pyrrolidone, 3 mols of water are generated, and in the conversion of beta-cyanopropionic acid to 2-pyrrolidone, 1 mol of water will be formed, while in the conversion of beta-cyanopropionamide to 2-pyrrolidone, one mol of ammonia will be formed, but no water.

The amount of hydrogen which is fed to the hydrogenation reaction zone preferably is sufficient so that there is between 2:1 and 200:1 mols of hydrogen per mol of succinic reactant, that is per mol of the hydrolyzed succinonitrile feed to the hydrogenation zone. In any case, preferably sufficient hydrogen is fed to maintain an appreciable hydrogen partial pressure on top of that required to maintain liquid phase reaction conditions for the succinic reactant in the presence of liquid water. The elevated pressure preferably is between 500 and 2500 psig, more preferably between 1000 and 2000 psig.

Suitable hydrogenation catalysts for the hydrogenation step include the Group VIII metals, namely, iron, cobalt, nickel, ruthenium, rhodium, palladium, osmium, iridium, and platinum. Preferred Group VIII hydrogenation metals include cobalt, nickel, ruthenium, rhodium, palladium, iridium, and platinum. Particularly preferred Group VIII metals are cobalt, nickel, palladium, and ruthenium.

The Group VIII metal preferably is supported, for example, on an inorganic refractory material such as alumina or silica or alumina-silica mixtures. Zirconia is a particularly preferred support.

Raney cobalt or Raney nickel catalysts can be used for the hydrogenation step. The Raney cobalt or Raney nickel are prepared in accordance with the known methods for preparing these hydrogenation catalysts.

A particularly preferred hydrogenation catalyst is ruthenium on refractory support such as alumina, silica, silica-alumina, carbon, or zirconia. A particularly preferred supported ruthenium catalyst is ruthenium on zirconia as described in more detail in commonly assigned application of H. Y. Lew and W. Alan Sweeney, titled "Preconditioned Ruthenium Catalysts And Processes For Preparing Pyrrolidone" and filed Mar. 17, 1978, the disclosure of which application is incorporated herein by reference.

Preferred amounts of the Group VIII metal or metals on the above-mentioned supports are 0.1 to 25 weight percent, more preferably 0.2 to 10 weight percent.

Preferably, the amount of catalyst used in the hydrogenation reaction zone is 0.01 to 5.0, more preferably 0.02 to 20 parts by weight of the succinic reactant feed.

EXAMPLES

To a 5-gallon stirred stainless steel autoclave there was charged 21.25 mols of succinonitrile, 4.6 mols of succinic anhydride, and 352 mols of water. It was charged at room temperature and then heated to 210° C. The contents were held at this temperature, and at a pressure of about 240 psig, with stirring for about 3 hours.

Succinic anhydride was included as an acid catalyst for the hydrolysis; however, other laboratory runs determined that this was not required.

A 2000 gram portion of the reaction product, that is, of the total effluent from the above 5-gallon reactor, was charged to a one-gallon reactor at room temperature. A hydrogenation catalyst in the amount of 150 grams of 1.8 weight percent ruthenium on zirconia was charged to the one-gallon reactor in the form of a powder. The reactor was pressurized with added hydrogen gas at room temperature to a pressure between 1500 and 1900 psig.

The reactor was then heated to 235° C. with stirring of the contents. The temperature was held at 235° C. for about 20 hours.

The product from this hydrogenation step was chromatographically analyzed; the yield of 2-pyrrolidone was 89 mol percent based on succinonitrile fed to the hydrolysis step.

In a repeat run on the hydrogenation step, a yield of about 90 mol percent was obtained, thus confirming the previous high yield of 89 percent. In this repeat run, a one-liter reaction vessel was used for the hydrogenation step and the feed was a portion of the total reaction product from the 5-gallon hydrolysis step as previously described. The reaction conditions for this repeat hydrogenation run were generally similar except that a residence time of only 12 hours was used for the hydrogenation step.

What is claimed is:

1. A process for producing 2-pyrrolidone which comprises
    (a) contacting succinonitrile with water at a temperature between 150° and 300° C. and a pressure between 100 and 10,000 psig to thereby hydrolyze succinonitrile; and
    (b) contacting the hydrolyzed succinonitrile with hydrogen in the presence of a heterogeneous hydrogenation catalyst and at a temperature between 200° and 300° C. and a pressure between 100 and 10,000 psig to thereby obtain 2-pyrrolidone.

2. A process in accordance with claim 1 wherein step (b) is carried out in the presence of at least 0.10 mol ammonia per mol of hydrolyzed succinonitrile and between 1 and 400 mols of water per mol of hydrolyzed succinonitrile.

3. A process in accordance with claim 2 wherein the hydrolysis is carried out at 180°–250° C.

4. A process in accordance with claim 2 wherein the hydrolysis conditions are adjusted to convert at least a portion of the succinonitrile to succinic acid in step (a).

5. A process in accordance with claim 2 wherein the catalyst used for step (b) comprises a Group VIII metal.

6. A process in accordance with claim 2 wherein the catalyst is a Group VIII metal on an inorganic porous carrier.

7. A process in accordance with claim 2 wherein the catalyst is ruthenium on a zirconia support.

* * * * *